US005693615A

United States Patent [19]
Stone

[11] Patent Number: 5,693,615
[45] Date of Patent: Dec. 2, 1997

[54] THERAPEUTIC COMPOSITIONS FOR OSTEOINDUCTION

[75] Inventor: Roger Lee Stone, Hamilton, Ohio

[73] Assignee: The Procter & Gamble Company, Cincinnati, Ohio

[21] Appl. No.: 377,292

[22] Filed: Jan. 23, 1995

Related U.S. Application Data

[63] Continuation of Ser. No. 243,435, May 13, 1994, abandoned, which is a continuation of Ser. No. 117,367, Sep. 7, 1993, abandoned, which is a continuation-in-part of Ser. No. 988,363, Dec. 9, 1992, abandoned, which is a continuation of Ser. No. 856,110, Mar. 27, 1992, abandoned, which is a continuation-in-part of Ser. No. 709,621, Jun. 5, 1991, abandoned.

[51] Int. Cl.$^6$ .......................... A61K 31/59; A61K 35/32
[52] U.S. Cl. ........................ 514/12; 514/21; 514/167; 530/350; 530/840
[58] Field of Search ...................... 514/12, 21, 167; 530/350, 840, 399

[56] References Cited

U.S. PATENT DOCUMENTS

| | | | |
|---|---|---|---|
| 4,294,753 | 10/1981 | Urist | 260/112 R |
| 4,434,894 | 3/1984 | Seyedin et al. | 260/112 R |
| 4,455,256 | 6/1984 | Urist | 260/112 R |
| 4,526,909 | 7/1985 | Urist | 523/115 |
| 4,563,350 | 1/1986 | Nathan et al. | 424/95 |
| 4,563,489 | 1/1986 | Urist | 524/21 |
| 4,596,574 | 6/1986 | Urist | 623/16 |
| 4,619,989 | 10/1986 | Urist | 530/417 |
| 4,627,982 | 12/1986 | Seyedin et al. | 424/95 |
| 4,698,328 | 10/1987 | Neer et al. | 514/12 |
| 4,761,471 | 8/1988 | Urist | 530/350 |
| 4,774,322 | 9/1988 | Seyedin et al. | 530/353 |
| 4,789,663 | 12/1988 | Wallace et al. | 514/21 |
| 4,789,732 | 12/1988 | Urist | 530/350 |
| 4,795,804 | 1/1989 | Urist | 530/350 |
| 4,804,744 | 2/1989 | Sen | 530/350 |
| 4,810,691 | 3/1989 | Seyedin et al. | 514/2 |
| 4,843,063 | 6/1989 | Seyedin et al. | 514/2 |
| 4,861,757 | 8/1989 | Antoniades et al. | 514/21 |
| 4,877,864 | 10/1989 | Wang et al. | 530/324 |
| 4,968,590 | 11/1990 | Kubersampath et al. | 530/326 |
| 5,002,583 | 3/1991 | Pitaru | 623/66 |
| 5,002,770 | 3/1991 | Kubersampath et al. | 424/423 |
| 5,011,691 | 4/1991 | Oppermann et al. | 424/423 |
| 5,013,649 | 5/1991 | Wang et al. | 435/69.1 |
| 5,035,901 | 7/1991 | Anderson et al. | 424/573 |
| 5,053,401 | 10/1991 | Matsumoto et al. | 514/167 |
| 5,073,373 | 12/1991 | O'Leary et al. | 424/422 |
| 5,106,626 | 4/1992 | Parsons et al. | 424/423 |
| 5,106,748 | 4/1992 | Woxney et al. | 435/252.3 |
| 5,108,922 | 4/1992 | Wang et al. | 435/240.2 |
| 5,116,738 | 5/1992 | Wang et al. | 435/69.1 |
| 5,118,667 | 6/1992 | Adams et al. | 514/12 |
| 5,141,905 | 8/1992 | Rosen et al. | 435/69.1 |
| 5,166,058 | 11/1992 | Wang et al. | 435/69.1 |
| 5,168,050 | 12/1992 | Hammonds, Jr. et al. | 435/69.1 |
| 5,169,837 | 12/1992 | Lagarde et al. | 514/21 |
| 5,187,076 | 2/1993 | Wozney et al. | 435/69.1 |

FOREIGN PATENT DOCUMENTS

| | | | |
|---|---|---|---|
| 2000498 | 10/1989 | Canada . | |
| 148 155 | 7/1985 | European Pat. Off. | C07K 15/06 |
| 309 241 | 3/1989 | European Pat. Off. | A61K 25/00 |
| 336 760 | 10/1989 | European Pat. Off. | C07K 7/00 |
| 349 048 | 1/1990 | European Pat. Off. | A61K 35/28 |
| 384 731 | 8/1990 | European Pat. Off. | A61K 35/28 |
| 409 472 | 1/1991 | European Pat. Off. | C12N 15/12 |
| 416 578 | 3/1991 | European Pat. Off. | C12N 15/12 |
| 89/09787 | 10/1989 | WIPO | C07K 13/00 |
| 89/09788 | 10/1989 | WIPO | C07K 13/00 |
| 89/10934 | 11/1989 | WIPO | C07K 7/08 |
| 91/18098 | 11/1991 | WIPO . | |

OTHER PUBLICATIONS

"Bone Morphogenic Proteins and Vitamin D", Nutrition Reviews, vol. 47, pp. 364–366 (1989).

Haussler, M.R., "Present Knowledge in Nutrition", Chapter 10, 4th Ed., The Nutrition Foundation, Inc., New York, (1976).

Sampath, T.K., S. Wientroub and A.H. Reddi, "Extracellular Matrix Proteins Involved in Bone Induction Are Vitamin D Dependent", Biochemical and Biophysical Communications, vol. 124, No. 3, pp. 829–835 (Nov. 1984).

Turner, R.T., J. Farley, J.J. Vandersteenhoven, S. Epstein, N.H. Bell and D.J. Baylink "Demonstration of Reduced Mitogenic and Osteoinductive Activities in Demineralized Allogeneic Bone Matrix from Vitamin D–deficient Rats", The Journal of Clinical Investigation, Inc., vol. 82, pp. 212–217 (Jul. 1988).

Underwood, J.L. and H.F. DeLuca, "Vitamin D is Not Directly Necessary for Bone Growth and Mineralization", American Journal of Physiology, vol. 246, pp. E493–E498 (1984).

Wang, E.A., V. Rosen, J.S. D'Alessandro, M. Bauduy, P. Cordes, T. Harada, D.I. Israel, R.M. Hewick, K.M. Kerns, P. LaPan, D.P. Luxenberg, D. McQuiid, I.K. Moutsatsos, J. Nove and J.M. Wozney, "Recombinant Human Bone Morphogenetic Protein Induces Bone Formation", Wang, Proc. Natl. Acad. Sci. USA, vol. 87, pp. 2220–2224 (Mar. 1990).

Weintroub, S. and A.H. Reddi, "Vitamin D Metabolites and Endochondral Bone Development", Int. Congr. Ser.–Excerpta Med., vol. 589, pp. 211–217 (1991).

Wozney, J.M., V. Rosen, A.J. Celeste, L.M. Mitsock, M.J. Whitters, R.W. Kriz, R.M. Hewick and E.A. Wang, "Novel Regulators of Bone Formation: Molecular Clones and Activities," Research Articles, Science, vol. 242, pp. 1528–1534 (Dec. 1988).

(List continued on next page.)

Primary Examiner—Chhaya D. Sayala
Attorney, Agent, or Firm—Brahm J. Corstanje; Bart S. Hersko; David L. Suter

[57] ABSTRACT

A method for generating new bone growth in a mammal comprising administrating to the mammal a safe and effective amount of a Vitamin D compound in combination with a safe and effective amount of osteoinductive extract or at least one BMP.

15 Claims, No Drawings

OTHER PUBLICATIONS

"Demonstration of Reduced Mitogenic and Osteoinductive Activities in Demineralized Allogeneic Bone Matrix from Vitamin D-deficient Rats", R.T. Turner et al., The Journal of Clinical Investigation, Inc., vol. 82, pp. 212–217 1988.

"Extracellular Matrix Proteins Involved in Bone Induction Are Vitamin D Dependent", T.K. Sampath et al., Biochemical and Biophysical Research Communications, vol. 124, pp. 829–835 1984.

"Vitamin D Is Not Directly Necessary for Bone Growth and Mineralization", J. L. Underwood & H. F. DeLuca, American Journal of Physiology, vol. 246, pp. E493–E498, (1984).

"Vitamin D Metabolites and Endochondral Bone Development", Weintroub, S. and A. H. Reddi, (1991) Int. Congr. Ser. –Excerpta Med., vol. 589, pp. 211–217.

"Present Knowledge in Nutrition", M.R. Haussler, 4th Ed., The Nutrition Foundation, Inc., New York, 1976.

"Recombinant Human Bone Morphogenetic Protein Induces Bone Formation", Wang, et al., Proc. Natl. Acad. Sci. USA, vol. 87, pp. 2220–2224, Mar. 1990.

"Novel Regulators of Bone Formation: Molecular Clones and Activities," Wozney et al., Research Articles, Science, vol. 242, pp. 1528–1534, 1988.

THERAPEUTIC COMPOSITIONS FOR OSTEOINDUCTION

This is a continuation of application Ser. No. 08/243,435, filed on May 13, 1994, which is a continuation of application Ser. No. 08/117,367, filed on Sep. 7, 1993, now both abandoned, which is a continuation-in-part of application Ser. No. 07/988,363, filed on Dec. 9, 1992 (now abandoned); which is a continuation of application Ser. No. 07/856,110, filed on Mar. 27, 1992 (now abandoned); which is a continuation-in-part of application Ser. No. 07/709,621, filed on Jun. 5, 1991 (now abandoned).

TECHNICAL FIELD

The present invention relates to the field of osteoinduction (bone growth). Specifically, the present invention relates to novel therapeutic formulations comprising the administration of bone morphogenetic proteins and a Vitamin D compound, resulting in synergistic bone growth.

BACKGROUND

In healthy individuals bone growth generally proceeds normally and fractures heal without the need for pharmacologic intervention. Nonetheless, in certain instances bones may be weakened or may fail to heal properly. For example, healing may proceed slowly in the elderly and in patients undergoing treatment with corticosteroids, such as transplant patients and those being treated for chronic lung disease. Another example is osteoporosis. Osteoporosis is an abnormal loss of bony tissue often occurring in postmenopausal woman and elderly men. The disorder increases the risks of small fractures occurring in the bones, particularly the spine. At present, osteoporosis is treated mainly by supplements of calcium, vitamin D, estrogen, or calcitonin, a hormone which controls the body's use of calcium. Unfortunately, these treatments are merely preventative against the further loss of bone. There is a need in the art for treatments that go beyond the prevention of bone loss and promote bone formation and/or reverse bone loss.

(1989) "Bone Morphogenic Proteins and Vitamin D", *Nutrition Reviews,* Vol. 47, pp. 364–366 concludes that Vitamin D in the diet prevents the loss of the osteoinductive activity of bone matrix.

Turner, R. T., J. Farley, J. J. Vandersteenhoven, S. Epstein, N. H. Bell, and D. J. Baylink, (1988) "Demonstration of Reduced Mitogenic and Osteoinductive Activities in Demineralized Allogeneic Bone Matrix from Vitamin D-deficient Rats", *The Journal of Clinical Investigation, Inc.,* Vol. 82, pp. 212–217, discloses the implantation of demineralized bone matrix from Vitamin D-deficient rats into normal rats. The demineralized bone matrix from Vitamin D-deficient rats did not promote osteoinduction as effectively as demineralized bone matrix from normal rats.

Sampath, T. K., S. Weintraub, and A. H. Reddi, (1984) "Extra-cellular Matrix Proteins Involved in bone Induction are Vitamin D Dependent", *Biochemical and Biophysical Research Communications,* Vol. 124, pp. 829–835, discloses a study involving implantation of demineralized bone matrix from normal rats and demineralized bone matrix from rachitic rats wherein the rachitic bone matrix did not induce bone growth while the normal bone matrix did. The study concluded that these results demonstrate that Vitamin D is necessary to produce bone inductive proteins in the bone matrix of a living rat.

U.S. Pat. No. 4,761,471, Urist, assigned to the Regents of the University of California, issued Aug. 2, 1988, discloses a bone morphogenetic protein composition comprising BMP factor and BMP associated protein having a molecular weight of 34,000 daltons. Use of such factors and compositions to induce bone formation in mammals is also disclosed.

U.S. Pat. No. 4,455,256, Urist, assigned to the Regents of the University of California, issued Jun. 19, 1984, discloses a bone morphogenetic protein having a molecular weight in the range of 1,000 to 100,000 daltons.

Various other bone morphogenetic proteins/factors, osteoinductive factors, osteogenic factors and other proteins/factors related to bone growth are disclosed in the following publications: U.S. Pat. No. 4,968,590, Kubersampath and Rueger, issued Nov. 6, 1990; U.S. Pat. No. 4,698,328, Neer, Potts and Slovik, issued Oct. 6, 1987; U.S. Pat. No. 4,877,864, Wang, Wozney and Rosen, issued Oct. 31, 1989; U.S. Pat. No. 4,861,757, Antoniades, Lynch and Williams, issued Aug. 29, 1989; U.S. Pat. No. 4,810,691, Seyedin, Thomas, Bentz, Ellingsworth and Armstrong, issued Mar. 7, 1989; U.S. Pat. No. 4,804,744, Sen, issued Feb. 14, 1989; U.S. Pat. No. 4,795,804, Urist, issued Jan. 3, 1989; U.S. Pat. No. 4,789,663, Wallace, Smestad, McPherson, Piez and Ross, issued Dec. 6, 1988; U.S. Pat. No. 4,789,732, Urist, issued Dec. 6, 1988; U.S. Pat. No. 4,774,322, Seyedin, Thomas, Bentz, Ellingsworth and Armstrong, issued Sep. 27, 1988; U.S. Pat. No. 4,698,328, Neer and Slovik, issued Oct. 6, 1987; U.S. Pat. No. 4,627,982, Seydin and Thomas, issued Dec. 9, 1986; U.S. Pat. No. 4,619,989, Urist, issued Oct. 28, 1986; U.S. Pat. No. 4,596,574, Urist, issued Jun. 24, 1986; U.S. Pat. No. 4,563,489, Urist, issued Jan. 7, 1986; U.S. Pat. No. 4,563,350, Nathan, Seyedin and Bentz, issued Jan. 7, 1986; U.S. Pat. No. 4,526,909, Urist, issued Jul. 2, 1985; U.S. Pat. No. 4,434,894, Seyedin and Thomas, issued Feb. 23, 1984; U.S. Pat. No. 4,294,753, Urist, issued Oct. 13, 1981; European Patent Application 349 048, Bab, Muhlrad, Gazit and Shteyer, published Jan. 3, 1990; European Patent Application 309 241, Chu, Nathan and Seyedin, published Mar. 29, 1989; European Patent Application 336 760, Bentz, Nathan, Rosen, Dasch and Seyedin, published Oct. 11, 1989; European Patent Application 145 155, Sen, published Jul. 10, 1985; World Patent Application 89/10934, Roos, Burns, Guy and McKnight, published Nov. 16, 1989; World Patent Applications 89/09787 and 89/09788, Oppermann, Kubersampath, Rueger and Ozkaynak, published Oct. 19, 1989; and World Patent Application 88/00205, Wang, Wozney and Rosen, published Jan. 14, 1988.

OBJECTS OF THE PRESENT INVENTION

It is an object of the present invention to provide a method for generating new bone growth in a mammal.

It is a further object of the present invention to provide a pharmaceutical composition which can be used to generate new bone growth in a mammal.

SUMMARY

The present invention relates to a method of generating new bone growth in mammals comprising administration to a mammal a combination of a safe and effective amount of a Vitamin D compound, and a safe and effective amount of one or more BMPs or osteoinductive extract comprising one or more BMPs.

The present invention further relates to a composition for generating new bone growth in mammals comprising a safe and effective amount of a Vitamin D compound; a safe and effective amount of a BMP or osteoinductive extract comprising one or more BMPs; and a pharmaceutically-acceptable carrier.

DETAILED DESCRIPTION

The present invention comprises the administration to a mammal of a combination of a safe and effective amount of a Vitamin D compound and a safe and effective amount of one or more BMPs or an osteoinductive extract comprising one or more BMPs. It has been determined that treatment with a Vitamin D compound, BMP or osteoinductive extract alone increases bone growth. Surprisingly, it has been further determined that treatment with a Vitamin D compound in combination with osteoinductive extract or in combination with at least one BMP results in a level of new bone growth greater than that achieved through administration of the BMP, osteoinductive extract or Vitamin D compound alone. Subjects in need of such treatment suffer from a variety of ailments which may be treated via this procedure, including but not limited to, bone fractures (closed and open), non-union fractures, congenital defects, as an adjunct in plastic surgery, in treating oncological resections, all diseases classified as osteoporosis, rheumetoid arthritis, osteoarthritis, septic arthritis, rickets, organic incorporation of prosthetic joints and dental implants, periodontal disease and defects, as well as osteopenic and osteomalacic conditions and disease.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "fracture reduction" means the restoration of a bone fracture by surgical or manipulative means to its normal anatomical relation.

As used herein, "BMP" means bone morphogenetic protein.

As used herein, "q.s." means quantity sufficient.

As used herein, all percentages are by weight unless otherwise specified.

As used herein "regional treatment" includes treating bone fractures (closed and open), treating non-union fractures, treating congenital defects, as an adjunct treatment to plastic surgery, treating oncological resections, organic incorporation of prosthetic joints, organic incorporation of dental implants, and treatment of periodontal disease and defects.

As used herein "systemic treatment" includes treating diseases classified as osteoporosis, rheumatoid arthritis, osteoarthritis, septic arthritis, rickets, and osteopenic conditions and diseases.

As used herein, all dose ranges for systemic treatment are recited as the dry weight of the actives per kg body weight of the mammal.

As used herein, all dose ranges for regional treatment are recited as the dry weight of the actives per $cm^2$ surface area of mineralized tissue to be treated.

As used herein, "mineralized tissue" means bone and teeth.

Vitamin D Compounds

One component involved in the method of the invention is a Vitamin D compound. As used herein, "Vitamin D compound" includes Vitamin D, ergocalciferol (Vitamin $D_2$), cholecalciferol (Vitamin $D_3$) and their biologically active metabolites and precursors. Preferred Vitamin D compounds include, but are not limited to, Vitamin $D_2$ (Sigma, St. Louis, Mo.); Vitamin $D_3$ (Sigma, St. Louis, Mo.); 1-α-hydroxy Vitamin $D_3$; 1-α-fluoro Vitamin $D_3$; 3-deoxy-1,25-dihydroxy Vitamin $D_3$; 25-hydroxy-5,6-trans Vitamin $D_3$; 25-hydroxy Vitamin $D_2$; 25-hydroxy Vitamin $D_3$ (Hoffman LaRoche); 1,25-dihydroxy Vitamin $D_2$; 24,25-dihydroxy Vitamin $D_2$; 24,25-dihydroxy Vitamin $D_3$ (Hoffman LaRoche); and 1,25-dihydroxy Vitamin $D_3$ (Duphar, Veenendaal, Holland). Preferably, the Vitamin D compound is selected from 25-hydroxy Vitamin $D_2$; 25-hydroxy Vitamin $D_3$; 1,25-dihydroxy Vitamin $D_2$; 24,25-dihydroxy Vitamin $D_2$; 24,25-dihydroxy Vitamin $D_3$; and 1,25-dihydroxy Vitamin $D_3$; more preferably 1,25-dihydroxy Vitamin $D_3$. Additional Vitamin D compounds useful in the present invention are well known to those skilled in the art and include, but are not limited to, those disclosed by the following U.S. Patents, each of which is incorporated herein by reference: U.S. Pat. No. 4,970,203, DeLuca and Kwiecinski, issued Nov. 13, 1990; U.S. Pat. No. 4,927,815, DeLuca, Kutner, Perlman and Schnoes, issued May 22, 1990; U.S. Pat. No. 4,857,518, DeLuca, Ikekawa and Tanaka, issued Aug. 15, 1989; U.S. Pat. No. 4,851,401, DeLuca, Kutner, Perlman and Schnoes, issued Jul. 25, 1989; U.S. Pat. No. 4,851,400, DeLuca, Ikekawa and Tanaka, issued Jul. 25, 1989; U.S. Pat. No. 4,847,012, DeLuca, Kutner, Perlman, Phelps, Schnoes and Sicinski, issued Jul. 11, 1989; U.S. Pat. No. 4,816,417, Dame, DeLuca and Pierce, issued Mar. 28, 1989; U.S. Pat. No. 4,769,181, DeLuca, Schnoes, Sicinski and Tanaka, issued Sep. 6, 1988; U.S. Pat. No. 4,755,329, DeLuca, Lee and Schnoes, issued Jul. 5, 1988; U.S. Pat. No. 4,719,205, DeLuca, Schnoes, Sicinski and Tanaka, issued Jan. 12, 1988; U.S. Pat. No. 4,719,204, DeLuca, Schnoes, Sicinski and Tanaka, issued Jan. 12, 1988; U.S. Pat. No. 4,717,721, DeLuca, Ikekawa, Ostrem and Schnoes, issued Jan. 5, 1988; U.S. Pat. No. 4,689,180, DeLuca, Schnoes, Sicinski and Tanaka, issued Aug. 25, 1987; U.S. Pat. No. 4,619,920, DeLuca, Ikekawa, Kobayashi and Tanaka, issued Oct. 28, 1986; U.S. Pat. No. 4,594,192, DeLuca, Ikekawa, Kobayashi and Tanaka, issued Jun. 10, 1986; U.S. Pat. No. 4,588,716, DeLuca and Schnoes, issued May 13, 1986; U.S. Pat. No. 4,588,528, DeLuca, Ikekawa and Tanaka, issued May 13, 1986; U.S. Pat. No. 4,564,474, DeLuca, Ikekawa, Kobayashi and Tanaka, issued Jan. 14, 1986; U.S. Pat. No. 4,555,364, DeLuca, Lee, Phelps and Schnoes, issued Nov. 26, 1985; U.S. Pat. No. 4,554,106, DeLuca, Lee, Phelps and Schnoes, issued Nov. 19, 1985; U.S. Pat. No. 4,552,698, DeLuca, Ikekawa, Kobayashi and Tanaka, issued Nov. 11, 1985; U.S. Pat. No. 4,512,925, DeLuca, Lee and Schnoes, issued Apr. 23, 1985; U.S. Pat. No. 4,505,906, DeLuca, Schnoes, Sicinski and Tanaka, issued Mar. 19, 1985; U.S. Pat. No. 4,502,991, DeLuca, Ikekawa, Kobayashi and Tanaka, issued Mar. 5, 1985; U.S. Pat. No. 4,500,460, DeLuca, Ikekawa, Kobayashi and Tanaka, issued Feb. 19, 1985; U.S. Pat. No. 4,481,198, Chu, DeLuca, Kabakoff and Schnoes, issued Nov. 6, 1984; U.S. Pat. No. 4,461,766, DeLuca, Hart and Schnoes, issued Jul. 24, 1984; U.S. Pat. No. 4,448,726, DeLuca, Paaren, Schnoes and Smith, issued May 15, 1984; U.S. Pat. No. 4,448,721, DeLuca, Morzycki and Schnoes, issued May 15, 1984; U.S. Pat. No. 4,428,946, DeLuca, Jorgensen and Schnoes, issued Jan. 31, 1984; U.S. Pat. No.

4,411,833, DeLuca, Ikekawa, Kobayashi and Tanaka, issued Oct. 25, 1983; U.S. Pat. No. 4,367,177, DeLuca, Schnoes and Wichman, issued Jan. 4, 1983; U.S. Pat. No. 4,358,406, DeLuca, Ikekawa, Kobayashi and Tanaka, issued Nov. 9, 1982; U.S. Pat. No. 4,338,312, DeLuca, Jorgensen and Schnoes, issued Jul. 6, 1982; U.S. Pat. No. 4,338,250, DeLuca, Hamer, Paaren and Schnoes, issued Jul. 6, 1982; U.S. Pat. No. 4,336,193, DeLuca, Fivizzani, Paaren, Schnoes and Wichmann, issued Jun. 22, 1982; U.S. Pat. No. 4,313,942, DeLuca, Frank, Paaren and Schnoes, issued Feb. 2, 1982; U.S. Pat. No. 4,307,231, DeLuca, Paaren, Schnoes, Tanaka and Wichmann, issued Dec. 22, 1981; U.S. Pat. No. 4,307,025, DeLuca, Ikekawa, Morisaki, Oshida, Schnoes and Tanaka, issued Dec. 22, 1981; U.S. Pat. No. 4,305,880, DeLuca, Ikekawa, Kobayashi and Tanaka, issued Dec. 15, 1981; U.S. Pat. No. 4,297,289, DeLuca, Fivizzani, Paaren and Schnoes, issued Oct. 27, 1981; U.S. Pat. No. 4,292,250, DeLuca, Levan and Schnoes, issued Sep. 29, 1981; U.S. Pat. No. 4,265,822, DeLuca, Hamer, Paaren and Schnoes, issued May 5, 1981; U.S. Pat. No. 4,264,513, DeLuca, Fivizzani, Napoli and Schnoes, issued Apr. 28, 1981; U.S. Pat. No. 4,263,214, DeLuca, Napoli, Onisko and Schnoes, issued Apr. 21, 1981; U.S. Pat. No. 4,260,804, DeLuca, Esvelt and Schnoes, issued Apr. 7, 1981; U.S. Pat. No. 4,260,549, DeLuca, Hamer, Paaren and Schnoes, issued Apr. 7, 1981; U.S. Pat. No. 4,254,045, DeLuca, Ikekawa, Morisaki, Oshida and Tanaka, issued Mar. 3, 1981; U.S. Reissue Pat. No. 30,538, DeLuca, Lam and Schnoes, issued Mar. 3, 1981; U.S. Pat. No. 4,248,791, DeLuca, Ikekawa, Kobayashi and Tanaka, issued Feb. 3, 1981; U.S. Pat. No. 4,234,495, DeLuca, Hamer, Paaren and Schnoes, issued Nov. 18, 1980; U.S. Pat. No. 4,230,627, DeLuca, Napoli, Onisko and Schnoes, issued Oct. 28, 1980; U.S. Pat. No. 4,229,359, Alper, DeLuca, Schnoes and Tanaka, issued Oct. 21, 1980; U.S. Pat. No. 4,229,358, DeLuca, Napoli, Onisko and Schnoes, issued Oct. 21, 1980; U.S. Pat. No. 4,229,357, DeLuca, Napoli, Onisko and Schnoes, issued Oct. 21, 1980; U.S. Pat. No. 4,226,788, DeLuca, Ikekawa, Kobayashi, Schnoes and Tanaka, issued Oct. 7, 1980; U.S. Pat. No. 4,226,787, DeLuca, Napoli, Onisko and Schnoes, issued Oct. 7, 1980; U.S. Pat. No. 4,224,231, Alper, DeLuca, Schnoes and Tanaka, issued Sep. 23, 1980; U.S. Pat. No. 4,224,230, DeLuca, Napoli, Onisko and Schnoes, issued Sep. 23, 1980; U.S. Pat. No. 4,223,131, DeLuca, Schnoes and Wichman, issued Sep. 16, 1980; U.S. Pat. No. 4,217,288, DeLuca, Onisko and Schnoes, issued Aug. 12, 1980; U.S. Pat. No. 4,209,634, DeLuca, Esvelt and Schnoes, issued Jun. 24, 1980; U.S. Pat. No. 4,202,829, DeLuca, Hamer, Paaren and Schnoes, issued May 13, 1980; U.S. Pat. No. 4,201,881, DeLuca, Ikekawa, Kobayashi, Schnoes and Tanaka, issued May 6, 1980; U.S. Pat. No. 4,196,133, DeLuca, Ikekawa, Kobayashi, Schnoes and Tanaka, issued Apr. 1, 1980; U.S. Pat. No. 4,195,027, DeLuca, Hamer, Paaren and Schnoes, issued Mar. 25, 1980; U.S. Pat. No. 4,188,345, DeLuca, Napoli, Oniski and Schnoes, issued Feb. 12, 1980; and U.S. Pat. No. 3,906,014, DeLuca, Lam and Schnoes, issued Sep. 16, 1975. Additional Vitamin D compounds useful in the present invention and disclosed by these references include, but are not limited to, hydroxylated 24-homo-vitamin D; cyclopentano-vitamin D; hydroxylated 26-homo-vitamin D; 1 α-hydroxy-vitamin D; 1-hydroxy-vitamin D; 1 α-hydroxy-vitamin $D_2$; 1 α,25-dihydroxy-22Z-dehydroxy-vitamin D; 26,26,26,27,27-pentafluoro-1 α-hydroxy-27-methoxy-vitamin $D_3$; 2 α-fluoro-vitamin $D_3$; 1,24-dihydroxy-delta 22-vitamin $D_3$; 23,23-difluoro-25-hydroxy-vitamin $D_3$; 1-hydroxy-3,5-cyclo-vitamin D; 23,23-di-fluoro-1 α,25-dihydroxy-vitamin $D_3$; 1,23-dihydroxy-vitamin D; hydroxy-vitamin $D_2$; 23,23-difluoro-1 α,25-dihydroxy-vitamin $D_3$; 23,23-difluoro-25-hydroxy-vitamin $D_3$; 26,26,26,27,27,27hexafluoro-1 α,25-dihydroxycholesterol; 23,25-dihydroxy-vitamin $D_3$; 26,26,26,27,27,27-hexafluoro-1 α,25-dihydroxycholecalciferol; 1 α,25-dihydroxy-2 β-fluoro-vitamin $D_3$; 24-fluoro-25-hydroxycholecalciferol; 5,6-trans-vitamin D; 1 α-hydroxy-25-keto-27-nor-cholecalciferol; fluoro-vitamin D; 1 α-hydroxy-2 β-fluorocholecalciferol; 3-deoxy-1 α-hydroxycholecalciferol; 25-hydroxy-26,26,26,27,27,27-hexafluorocholecalciferol; α-hydroxy-3,5-cyclovitamin D; 25-hydroxycholecalciferol; 24,24-difluoro-1 α,25-dihydroxycholecalciferol; 25-hydroxycholecalciferol; 25-hydroxycholecalciferol-26,23-lactone; 24,24-difluoro-1α,25-dihydroxycholecalciferol; 24,24-difluoro-25-hydroxycholecalciferol; 3,5-cyclo-vitamin D; and 3-deoxy-α-hydroxycholecalciferol. Additional Vitamin D compounds useful in the present invention further include those disclosed in *The Handbook of Vitamins*, L. J. Machlin, Ed., Mercel Dekker, Inc. (1984), incorporated herein by reference. Vitamin D compounds useful in the present invention disclosed by this reference, include, bur are not limited to, 1,25-dihydroxy Vitamin D, 3-deoxy-1,25-dihydroxy Vitamin D, 27-nor-25-hydroxy Vitamin $D_3$, 26,27-bis-nor-25-hydroxy Vitamin $D_3$ 24-nor-25-hydroxy Vitamin $D_3$, 25-hydroxy Vitamin D, 1,25-dihydroxy Vitamin D, 1α-hydroxy Vitamin $D_3$ and 25-fluoro-1α-hydroxy Vitamin $D_3$.

A safe and effective amount of a Vitamin D compound is dosed in combination with at least one BMP or in combination with an osteoinductive extract comprising at least one BMP.

A preferred dose range for administration of the Vitamin D compound for systemic treatment is from about 1 ng to about 1 mg, preferably from about 10 ng to about 500 mg, more preferably from about 20 ng to about 10 mg.

For purposes of regional treatment, the dose range of the Vitamin D compound is preferably from about 1 ng to about 1 mg, preferably from about 10 ng to about 500 ng, more preferably from about 10 ng to about 50 ng, most preferably from about 20 ng to about 30 ng.

Preferably, doses are administered over a 1 day to 6 month period, more preferably from about 1 week to about 1 month. Preferably doses are administered from about once per month to about 5 times per day, more preferably from about once per week to about once per day.

Bone Morphogenetic Proteins

In one embodiment of the present invention, a Vitamin D compound is administered in combination with one or more BMPs to generate new bone growth in a mammal. These BMPs are preferably selected from the group consisting of BMP-1, BMP-2, BMP-3, BMP-4, BMP-5, BMP-6 and BMP-7.

A safe and effective amount of a BMP, preferably selected from the group consisting of BMP-1, BMP-2, BMP-3, BMP-4, BMP-5, BMP-6 and BMP-7, is dosed in combination with a Vitamin D compound.

A preferred dose range for administration of the BMP for systemic treatment is from about 1 pg to about 100 mg, preferably from about 1 ng to about 10 mg, more preferably from about 10 ng to about 2.5 mg.

For purposes of regional treatment, a preferred dose range for the BMP is from about 1 pg to about 100 mg, more preferably from about 1.5 ng to about 90 mg, more preferably from about 1.8 ng to about 75 mg, more preferably from about 2 ng to about 50 mg, more preferably from about 2.2 ng to about 25 mg, more preferably still from about 2.3 ng to about 10 mg, most preferably from about 2.5 ng to about 5 mg. Preferably the dose range is at least about 2.5 ng.

Preferably, doses are administered over a 1 day to 6 month period, more preferably from about 1 week to about 1 month. Preferably doses are administered from about once per month to about 5 times per day, more preferably from about once per week to about once per day.

As used herein, "BMP-1" means a peptide encoded by a DNA sequence comprising SEQ ID NO:1. The DNA sequence encoding BMP-1 has ATCC No. 40311 (see ATCC/NIH REPOSITORY CATALOGUE OF HUMAN AND MOUSE DNA PROBES AND LIBRARIES, sixth Edition, 1992, p. 57, hereinafter "ATCC/NIH REPOSITORY CATALOGUE"). Isolation of BMP-1 is disclosed in U.S. Pat. No. 4,877,864, Wang, Wozney and Rosen, issued Oct. 31, 1989; and U.S. Pat. No. 5,108,922, Wang, Wozney and Rosen, issued Apr. 28, 1992; both of which are incorporated herein by reference.

As used herein, "BMP-2" means a peptide encoded by a DNA sequence comprising SEQ ID NO:2. The DNA sequence encoding BMP-2 has ATCC No. 40345 (see ATCC/NIH REPOSITORY CATALOGUE). Isolation of BMP-2 is disclosed in U.S. Pat. No. 5,013,649, Wang, Wozney and Rosen, issued May 7, 1991; U.S. Pat. No. 5,166,058, Wang, Wozney and Rosen, issued Nov. 24, 1992; and U.S. Pat. No. 5,168,050, Hammonds and Mason, issued Dec. 1, 1992; each of which is incorporated herein by reference. Preferably the ratio of BMP-2 to Vitamin D dosed is from about 1:83 to about 1:167. In one embodiment of the present invention, 500 ng of BMP-2 is dosed with 6 ng of 1,25 dihydroxy Vitamin $D_3$. In another embodiment of the present invention, 1000 ng of BMP-2 is dosed with 6 ng of 1,25 dihydroxy Vitamin $D_3$.

As used herein, "BMP-3" means a peptide encoded by a DNA sequence comprising SEQ ID NO:3. Isolation of BMP-3 is disclosed in U.S. Pat. No. 5,116,738, Wang, Wozney and Rosen, issued May 26, 1992, incorporated herein by reference.

As used herein, "BMP4" means a peptide encoded by a DNA sequence comprising SEQ ID NO:4. The DNA sequence encoding BMP-4 has ATCC No. 40342 (see ATCC/NIH REPOSITORY CATALOGUE). Isolation of BMP-4 is disclosed in U.S. Pat. No. 5,013,649, Wang, Wozney and Rosen, issued May 7, 1991, incorporated herein by reference. Preferably the ratio of BMP-4 to Vitamin D dosed is from about 1:10. In one embodiment of the present invention, 62.5 ng of BMP-4 is dosed with 6 ng of 1,25 dihydroxy Vitamin $D_3$.

As used herein, "BMP-5" means a peptide encoded by a DNA sequence comprising SEQ ID NO:5. Isolation of BMP-5 is disclosed in U.S. Pat. No. 5,106,748, Wozney, Rosen and Wang, issued Apr. 21, 1992, incorporated herein by reference.

As used herein, "BMP-6" means a peptide encoded by a DNA sequence comprising SEQ ID NO: 6. Isolation of BMP-7 is disclosed in U.S. Pat. No. 5,141,905, Rosen, Wang, and Wozney, issued Aug. 25, 1992, incorporated herein by reference.

As used herein, "BMP-7" means a peptide encoded by a DNA sequence comprising SEQ ID NO: 7. Isolation of BMP-7 is disclosed in U.S. Pat. No. 5,141,905, Rosen, Wang, and Wozney, issued Aug. 25, 1992, incorporated herein by reference.

As used herein, "A", "T", "G", and "C" refer to the nucleotides containing adenine, thymine, guanine and cytosine respectively.

Osteoinductive Extract

Another component of the invention is an osteoinductive extract. As used herein, "osteoinductive extract" means a chemical extract of bone, comprising one or more various bone morphogenetic proteins, including, but not limited to, BMP-1, BMP-2, BMP-3, BMP-4, BMP-5, BMP-6 and BMP-7, wherein each BMP has a molecular weight of from about 28,000 to about 40,000 daltons.

The 28,000 to 40,000 dalton molecular weight range is in reference to the BMP's dimer weight. Preferably, the molecular weight of the dimer is from about 30,000 to about 34,000 daltons. The BMP dimer comprises two monomers, each having a molecular weight of from about 14,000 to about 20,000 daltons, preferably from about 15,000 to about 17,000 daltons.

A preferred method of obtaining the osteoinductive extract is as follows:

Snip the skin at the ankles of a 7–8 week old Long-Evans rat (Charles River laboratories, Wilmington, Mass.). Remove both tibiae and place in cold water. Rinse the bone with distilled water to remove non-osseous tissue (tissue other than bone). Allow the bone to air dry. Grind the bones by placing in an Osterizer (Oster Commercial, Milwaukee, Wis.) blender with water and ice. With the blender set at "liquefy" speed, continue to add bone. Allow the blended material to settle for a few minutes. Decant the liquid layer. Place the solid layer on a stirring plate and add distilled water to wash. Continue washing until the distilled water washes clear. Once the distilled water is clear, add ice and stir. Add 1 ml of 1 mM of phenylmethylsulfonyl fluoride (PMSF). Wash for 1 hour adding ice frequently. Repeat with a second water wash. Place the sample in an ice water bath on a stirring plate. Defat with absolute ethanol, then defat twice with ethyl ether. Spread bone material onto glass petri dishes. Allow the bone chips to air dry overnight.

Weigh the bone chips following the overnight drying, Using a sieve (U.S.A. Standard Sieve Series, Newark Wire Cloth Co., Newark, N.J.; sieve #40 retains particles greater than 425 mm and sieve #170 retains particles greater than 90 mm), isolate the bone particles in the 90–425 um range. Grind any particles greater than 425 mm in a MicroMill (Scienceware Bel-Art Products, Pequannock, N.J.) for 1 minute adding dry ice to the bone particles to keep the material cold. Repeat the sieving and MicroMill grinding steps of the greater than 425 mm particles until the amount of total recovery is greater than ⅔ of the initial weight of the bone. Store the particles at 4° C. until the next step. Weigh the particles isolated thus far. For each gram of particles, add 25 ml of 0.6N HCl. Stir vigorously at 4° C. for 2 hours. After 2 hours, stop stirring and allow the particles to settle. Decant the HCl. Add fresh 0.6N HCl and stir again for 2 hours. Decant the HCl and add fresh 0.6N HCl a third time and stir for two hours. Decant the HCl and rinse with distilled water. Using litmus paper, check the pH of the water for the presence of HCl. Continue rinsing with distilled water until the pH is between about 5 and 5.5. Rinse the bone particles with ethanol three times. Swirl, allow to settle, and remove the supernatant. Rinse the bone particles with ethyl ether three times as above. Dry overnight in glass plates. The dried bone particles are referred to as "acid demineralized bone particles".

The acid demineralized bone particles are deproteinized as follows: Weigh the material following the overnight drying. For each gram of material, add a solution of 30 ml 4M guanidine-HCl, 10 mM Tris and 1.0 mM PMSF pH 6.4 to the bone material in a beaker. Extract for 16 hours at 4° with vigorous stirring. Following the 16 hour extraction, cease stirring and allow the material to settle. Pour off the guanidine solution and save. Extract the material a second time for 6–7 hours using fresh guanidine-HCl solution. Following the extraction, pour off the solution and combine with the previously saved solution. The bone particles are now demineralized and deproteinized.

Dialyze the saved guanidine-HCl solution against distilled $H_2O$ at 4° C. using 50 mm dialysis tubing (3500 molecular weight cutoff). Following dialysis, lyopholize the material and resolubilize the lyophilized material in 4M Urea-0.05M Tris-0.1M NaCl, pH 7.4. Mix the solubilized material in a conical centrifuge tube with Heparin-Agarose and mix overnight on a rotator at 4° C. Pour the Heparin-Agarose slurry into a column. Wash with 1 column volume 4M urea, 0.05M Tris, 0.1M NaCl, pH 7.4 buffer. Collect the fraction. Wash with 3 column volumes of 4M urea, 0.05M Tris, 0.2M NaCl, pH 7.4 buffer. Step off the material with 3 column volumes of 4M urea, 0.05M Tris, 0.75M NaCl, pH 7.4. Concentrate this sample in a 50 ml Amicon concentrator (Amicon Corp., Danvers, Mass.) with filter (10,000 molecular weight cut off) to about 4–5 ml. Assay for protein concentration using BCA (bicinchoninic acid) Protein Assay Reagent (Pierce, Rockford, Ill.) and dialyze (3500 molecular weight cutoff dialysis tubing) in 4M guanidine-0.01M Tris pH 7.4. Load material on Sephacryl S-200 column and collect fractions. The fractions containing the major protein peak are dialyzed against 1M acetic acid and assayed for activity.

Active fractions from the gel filtration are combined and dialyzed against three changes of 6M urea, 25 mM Na acetate, pH 4.6. The dialysate is loaded onto a column of carboxymethyl-sepharose (CM-Sepharose) equilibrated with the same buffer. The column is washed with 6M urea, 25 mM Na acetate, pH 4.6 and activity eluted using a 0–0.5M NaCl gradient. Fractions are analyzed for protein concentration and sodium dodecyl sulfate gel electrophoresis. The activity located in the seven fractions before and after the beginning of the major protein peak are pooled for further purification.

The pooled CM-Sepharose fractions are dialyzed three times for 24 hours each against 1% acetic acid. The dialysate is lyophilized to dryness and the protein pellet dissolved into 30 ml of 6M urea, 0.5M NaCl, 25 mM Na phosphate, pH 7.4. The sample is applied on a column of chelating Sepharose charged with zinc and equilibrated with the above buffer. The column is washed with the above buffer and then eluted with a gradient from 6M urea, 0.5M NaCl, 25 mM Na phosphate, pH 7.4 to 6M urea, 0.5M NaCl, 25 mM Na acetate, pH 4.6. Aliquots of each fraction are labeled with 125I and analyzed by SDS gel electrophoresis. Aliquots (100 ml) of each fraction are combined with 400 ml of elution buffer, dialyzed against 1% acetic acid and assayed for activity. Highly purified molecular weight range ($M_r$) 25–40 kD peptides are assayed in the bone induction assay.

A safe and effective amount of osteoinductive extract is dosed in combination with a Vitamin D compound. For purposes of systemic treatment, the osteoinductive extract dosed preferably comprises at least one BMP in an amount from about 1 pg to about 100 mg, preferably from about 1 ng to about 10 mg, more preferably from about 10 ng to about 2.5 mg.

For purposes of regional treatment, the osteoinductive extract dosed preferably comprises at least one BMP in an amount from about 1 pg to about 100 mg, more preferably from about 1.5 mg to about 90 mg, preferably from about 1.8 mg to about 75 mg, more preferably from about 2.0 mg to about 50 mg, more preferably still from about 2.2 mg to about 25 mg, more preferably from about 2.3 mg to about 10 mg, most preferably from about 2.5 mg to about 5 mg. Preferably the dose range is at least about 2.5 mg.

Preferably, doses are administered over a 1 day to 6 month period, more preferably from about 1 week to about 1 month. Preferably doses are administered from about once per month to about 5 times per day, more preferably from about once per week to about once per day.

Pharmaceutically Acceptable Carrier

The Vitamin D compound, osteoinductive extract, or BMP may be administered via a pharmaceutically acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being commingled with the compound(s) of the subject invention, and with each other in a manner such that there is no interaction which would substantially reduce the pharmaceutical efficacy of the pharmaceutical composition under ordinary usage situations. Pharmaceutically-acceptable carriers must, of course, be of sufficiently high purity and sufficiently low toxicity to render them suitable for administration to human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; phosphate buffer solutions; cocoa butter (suppository base); emulsifiers, such as the TWEENS®; as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., NSAI drugs; pain killers; muscle relaxants) may be included in the pharmaceutically-acceptable carrier for use in the compositions of the present invention. For example, art-known local anesthetics may be included in the pharmaceutically-acceptable carrier (e.g., benzyl alcohol; NOVOCAINE®; lidocaine).

Additional examples of carriers include collagen, demineralized bone particles, ceramic and metallic implant materials, collagen membrane and bone grafts (isogenic or allogenic).

The choice of a pharmaceutically-acceptable carrier to be used in conjunction with the compounds of the present invention is determined by the way the compound is to be administered. The preferred modes of administering the compounds of the present invention are by injection, oral administration, topical-oral administration, and nasopharyngeal administration or a combination of modes (i.e., osteoinductive extract via injection and Vitamin D compound via oral administration). If the compound is to be injected, the preferred pharmaceutically-acceptable carrier is sterile, physiological saline. Suitable pharmaceutically-acceptable carriers for oral administration include those suited for tablets, and capsules. Suitable pharmaceutically-acceptable carriers for topical-oral administration include those suited for pastes, gels, and liquids. Suitable pharmaceutically-acceptable carriers for nasopharyngeal administration include those suited for drops, sprays, mists and powders.

A separate pharmaceutically-acceptable carrier may be used in conjunction with each active component of the present invention or a single pharmaceutically-acceptable carrier may be employed in conjunction with a mixture of the active components of the present invention. In either case, the pharmaceutically-acceptable carrier is used at a concentration sufficient to provide a practical size to dosage relationship. The pharmaceutically-acceptable carriers, in total, may comprise from about 0.1% to about 99.99999% by weight of the pharmaceutical compositions of the present invention, preferably from about 50% to about 99.999%, and most preferably from about 75% to about 99.9%.

Specific oral and injectable carriers useful in this invention are described in the following U.S. Patents, all incorporated by reference herein: U.S. Pat. No. 4,401,663, Buckwalter, et al, issued Aug. 30, 1983; U.S. Pat. No. 4,424,205, LaHann, et al, issued Jan. 31, 1984; U.S. Pat. No. 4,443,473, Buckwalter, et al, issued Apr. 12, 1984; U.S. Pat. No. 4,493,848, LaHann, et al, issued Jan. 15, 1984. Representative pharmaceutical compositions of the present invention are provided in the Examples hereinafter.

Pharmaceutically-acceptable carriers suitable for the preparation of unit dosage forms for oral administration, topical-oral administration, nasopharyngeal administration and injection are well-known in the art. Their selection will depend on secondary considerations like taste, cost, and/or shelf stability, which are not critical for the purposes of the present invention, and can be made without difficulty by a person skilled in the art. Pharmaceutically-acceptable carriers useful in the compositions of the present invention are described more fully hereinafter.

A. Oral Dose Forms

Preferably, the vitamin D compound is administered via an oral dose form. Various oral dosage forms can be used, including such solid forms as tablets, capsules, granules, bulk powders and microcapsules of the drug. These oral forms comprise a safe and effective amount, usually at least about 0.5%, and preferably from about 1% to about 10% of the compound of the present invention. Tablets can be compressed, enteric-coated, sugar-coated or filmcoated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin and propylene glycol. Specific examples of pharmaceutically-acceptable carriers and excipients that may be used in formulating oral dosage forms containing compounds of the present invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," MODERN PHARMACEUTICS, Vol. 7, (Banker and Rhodes, editors), 359–427 (1979), incorporated herein by reference. Techniques and compositions for making tablets (compressed, formulas and molded), capsules (hard and soft gelatin) and pills are described in REMINGTON'S PHARMACEUTICAL SCIENCES (Arthur Osol, editor), 1553–1593 (1980), incorporated herein by reference.

B. Topical-oral Dose Forms

"Topical-oral carrier", as used herein, denotes a carrier for the component of interest which results in a composition which is administered topically to the oral cavity, held therein for a period of time, and then is largely expectorated rather than being swallowed. Such compositions include toothpastes, tooth gels, tooth powders, mouthwashes, mouthsprays, prophylaxis pastes, dental treatment solutions, biogels or other sustained release products, and the like.

Components of the topical-oral carrier are suitable for administration to the oral cavity of a human or lower animal and are compatible with one another and the other components, especially the Vitamin D compound and osteoinductive extract or BMP, used in an oral composition of the subject invention. Preferred topical-oral carriers thus provide the desired characteristics for toothpastes, tooth gels, tooth powders, mouthwashes, mouthsprays, prophylaxis pastes, dental treatment solutions, and the like. The topical-oral carriers of the subject invention comprise components typically used in such compositions which are well known to a skilled practitioner. Such components include, but are not limited to anticaries agents, antiplaque agents, anticalculus agents, dental abrasives, surfactants, flavoring agents, sweetening agents, binders, humectants, thickening agents, buffering agents, preservatives, coloring agents and pigments, ethanol, and water.

Preferred compositions of the subject invention are in the form of toothpastes. Components of such toothpastes generally include a dental abrasive (from about 10% to about 50%), a surfactant (from about 0.5% to about 10%), a thickening agent (from about 0.1% to about 5%) a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0.3% as fluoride ion), an anticalculus agent (from about 0.1% to about 13%), and an antiplaque agent (from about 0.1% to about 5%).

Other preferred compositions of the subject invention are mouthwashes and mouthsprays. Components of such mouthwashes and mouthsprays include water (from about 45% to about 95%), ethanol (from about 0% to about 25%), a humectant (from about 0% to about 50%), a surfactant agent (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouthsprays may also include one or more of an anticaries agent (from about 0.05% to about 0.3% as fluoride ion), an anticalculus agent (from about 0.01% to about 3%), and an antiplaque agent (from about 0.1% to about 5%).

Other preferred compositions of the subject invention are dental solutions. Components of such dental solutions generally include water (from about 90% to about 99%), preservative (from about 0.01% to about 0.5%), thickening agent (from about 0% to about 5%), flavoring agent (from about 0.04% to about 2%), sweetening agent (from about 0.1% to about 3%), and surfactant (from 0% to about 5%).

"Topical-oral carrier" as used herein, also denotes fibers, strips or tubes which can be impregnated with the active components of the present invention and inserted or implanted into a periodontal pocket. Such compositions of the subject invention can readily be achieved by one of ordinary skill in the art using the teachings disclosed hereinbefore, the following references, incorporated herein by reference, and related well-known technologies: U.S. Pat. No. 4,666,897 issued to Golub, McNamara & Ramamurthy on May 19, 1987; European Patent Application No. 244,118 A1 in the name of Baker, published on Nov. 4, 1987; European Patent Application No. 286,802 A2 in the name of Kametaka, Miyazaki, Hayashi, Handa & Kameda, published Oct. 19, 1988; Addy, M., L. Rawle, R. Handley, H. Newman & J. Coventry, "The development and in vitro evaluation of acrylic strips and dialysis tubing for local drug delivery", JOURNAL OF PERIODONTOLOGY, Vol. 53 (1982), pp. 693–698; Goodson, J. M., A. D. Haffajee & S. S. Socransky, "Periodontal therapy by local delivery of tetracycline, JOURNAL OF CLINICAL PERIODONTOLOGY, Vol. 6 (1979), pp. 83–92; Goodson, J., D. Holborow, R. Dunn, P. Hogan & S. Dunham, "Monolithic tetracycline containing fibers for controlled delivery to periodontal pockets", JOURNAL OF PERIODONTOLOGY, Vol. 54 (1983), pp. 575–579; Dunn, R., J. Gibson, B. Perkins, J. Goodson & L. Laufe, "Fibrous delivery systems for antimicrobial agents", POLYMER SCIENCE AND TECHNOLOGY, Vol. 32 (1985), pp. 47–59; Dunn, R., J. Gibson, B. Perkins, J. Goodson & L. Laufe, "Fibrous delivery systems for antimicrobial agents", POLYMER MATERIAL SCIENCE ENGINEERING, Vol. 51 (1984), pp. 28–31; Olanoff, L. & J. Anderson, "Controlled release of tetracycline—III: A physiological pharmacokinetic model of the pregnant rat", JOURNAL OF PHARMACOKINETICS AND BIOPHARMACEUTICS, Vol. 8 (1980), pp. 599–620; Elkayam, R., M. Friedman, A. Stabholz, A. Soskolne, M. Sela & L. Golub, "Sustained release device containing minocycline for local treatment of periodontal disease", JOURNAL OF CONTROLLED RELEASE, Vol. 7 (1988), pp. 231–236; and Goodson, J., "Multi-center evaluation of tetracycline fiber therapy. I, Experimental Design", JOURNAL OF DENTAL RESEARCH, Vol. 68 (1989), p. 197; and references cited therein.

C. Injectable Dose Forms

The active components of the present invention are also useful when injected. The dosage of the active components of the present invention which is both safe and effective to provide bone growth activity will vary with the particular condition being treated, the severity of the condition, the duration of treatment, the specific mixture of compounds employed and its usage concentration, and like factors within the specific knowledge and expertise of the attending physician and commensurate with a reasonable benefit/risk ratio associated with the use of any drug compound. In addition, lower dosages will be utilized when only local or minor bone growth is desired, whereas higher dosages will be utilized when general or major bone growth is desired.

Methods and materials for manufacturing injectables can be found in REMINGTON'S PHARMACEUTICAL SCIENCES, 17Ed., 1985, Chapter 85, p. 1518, the disclosures of which are incorporated herein by reference in their entirety. Preferably, the injectable composition is an aqueous solution.

The aqueous solutions preferably consist of water (preferably from about 80% to about 99.999%), a suitable solubilizer, various types of acids, and an antimicrobial agent. Several solubilizers are known. Examples of such solubilizers are as follows: urea compounds (e.g., urea; urethan); surfactants (e.g., TWEENS®; Spans; sodium deoxycholate and Pluronics); cellulosic agents (e.g., carboxymethylcellulose); carbohydrates (e.g., sorbitol; mannitol); B vitamins (e.g., nicotinamide); xanthine derivatives; and alcohols (e.g., benzyl alcohol). Examples of acids to be used include the following: glucuronic; galacturonic; fumaric; gentisic; acetic; citric and lactobionic. Types of antimicrobial agents that can be used are the following: phenylmercuric nitrate; thimerosal; benzethonium chloride; benzalkonium chloride; phenol; cresol; and chlorobutanol. An art-known local anesthetic (e.g., benzyl alcohol; NOVOCAINE®; lidocaine) may also be included.

Preferably, the osteoinductive extract and the BMP's are administered via an injectable dose form.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE I

An injectable composition comprising the osteoinductive extract and an oral composition comprising 1,25-dihydroxy Vitamin $D_3$ for bone fracture repair is prepared by combining the following components utilizing conventional mixing techniques.

| Component | Percent by Weight of Composition |
|---|---|
| BMP composition | |
| BMP-1 | 0.04 |
| NaCl | 0.90 |
| Sterile water | q.s. |
| | 100.00 |
| 1,25-dihydroxy Vitamin $D_3$ composition | |
| 1,25-dihydroxy Vitamin $D_3$ | 0.01 |
| Corn starch | 18.49 |
| Lactose | 63.00 |
| Talc | 18.00 |
| Stearic acid | 0.50 |
| | 100.00 |

0.1 cc of the BMP composition is injected into the fracture site at the time of fracture reduction and once daily thereafter. 100 mg of the 1,25-dihydroxy Vitamin $D_3$ composition is orally administered 24 hours before fracture reduction and once daily thereafter. The BMP and 1,25-dihydroxy Vitamin $D_3$ are administered until desired repair is achieved, preferably over a seven day period.

EXAMPLE II

An injectable composition for bone fracture repair is prepared by combining the following components utilizing conventional mixing techniques.

| Component | Percent by Weight of Composition |
|---|---|
| BMP-2 | 0.04 |
| 25-hydroxy Vitamin $D_2$ | 0.01 |
| NaCl | 0.09 |
| Sterile water for injection | q.s. |
| | 100.00 |

0.1 cc of the composition is injected into the fracture site at the time of fracture reduction and once daily thereafter until desired repair is achieved.

EXAMPLE III

A composition for inducing bone growth following reconstructive surgery is prepared by combining the following components utilizing conventional mixing techniques.

| Component | Percent by Weight of Composition |
|---|---|
| BMP-3 | 0.04 |
| 1,25-dihydroxy Vitamin $D_2$ | 0.01 |
| NaCl | 0.90 |
| Sterile water | q.s. |
| | 100.00 |

0.1 cc of the composition per $cm^2$ of surface area of surgically reconstructed bone is deposited directly onto the bone surface.

EXAMPLE IV

A composition for accelerating the healing and providing a stronger bond between natural bone and an artificial prosthesis is prepared by combining the following components utilizing conventional mixing techniques.

| Component | Percent by Weight Composition |
|---|---|
| BMP-1 | 0.04 |
| BMP-2 | 0.04 |
| BMP-4 | 0.04 |
| 24,25-dihydroxy Vitamin $D_3$ | 0.01 |
| NaCl | 0.90 |
| Sterile water | q.s. |
| | 100.00 |

0.1 cc of the composition per $cm^2$ surface area of natural bone proximate to the prosthesis is deposited directly onto the natural bone.

EXAMPLE V

A topical oral carrier composition for periodontal therapy is prepared by combining the following components utilizing conventional mixing techniques.

| Component | Percent by Weight of Composition |
|---|---|
| BMP-2 | 0.04 |
| NaCl | 0.90 |
| Sterile water | q.s. |
| | 100.00 |

After the patient is prepared using conventional periodontal surgical therapy 0.1 cc of the composition per exposed tooth is deposited into the surgery site. Soft tissue flaps are then sutured to close the surgical site. This treatment is useful for restoring alveolar and supporting bone in the periodontium lost by disease.

EXAMPLE VI

An injectable composition comprising the BMPs 2, 3, 4 and 5 and an oral composition comprising 1,25-dihydroxy Vitamin $D_3$ for treatment of osteoporosis is prepared by combining the following components utilizing conventional mixing techniques.

| Component | Percent by Weight of Composition |
|---|---|
| osteoinductive extract composition | |
| BMP-2 | 0.001 |
| BMP-3 | 0.001 |
| BMP-4 | 0.001 |
| BMP-5 | 0.001 |
| NaCl | 0.900 |
| Sterile water | q.s. |
| | 100.000 |
| 1,25-dihydroxy Vitamin $D_3$ composition | |
| 1,25-dihydroxy Vitamin $D_3$ | 0.01 |
| Corn starch | 18.49 |
| Lactose | 63.00 |
| Talc | 18.00 |
| Stearic acid | 0.50 |
| | 100.00 |

1 cc of the BMP composition is injected intravenously once per day. 50 mg of the 1,25-dihydroxy Vitamin $D_3$ composition is orally administered within one hour of the osteoinductive extract injection and once daily thereafter. The osteoinductive extract and 1,25-dihydroxy Vitamin $D_3$ are administered over a 7-day period.

EXAMPLE VII

A composition for inducing bone growth of a non-union fracture is prepared by combining the following components utilizing conventional mixing techniques. As used herein, "non-union fracture" means a fracture that has failed to heal normally.

| Component | Percent by Weight of Composition |
|---|---|
| BMPA | 0.004 |
| 1,25-dihydroxy vitamin $D_3$ | 0.010 |
| Acid demineralized bone particles | 90.000 |
| NaCl | 0.900 |
| Sterile water for injection | q.s. |
| | 100.000 |

At the time of fracture reduction, a sufficient quantity of the above composition is deposited directly into the non-union site thereby filling in any bone deficit.

The invention has been described herein with reference to certain preferred embodiments and examples. Obvious variations may appear to those skilled in the art. Therefore, the invention is not to be considered limited thereto but only by the claims which follow.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2487 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
GCCGCTTCCC TCGCCGCCGC CCCGCCAGCA TGCCCGGCGT GGCCCGCCTG CCGCTGCTGC      60
TCGGGCTGCT GCTGCTCCCG CGTCCCGGCC GGCCGCTGGA CTTGGCCGAC TACACCTATG     120
ACCTGGCGGA GGAGGACGAC TCGGAGCCCC TCAACTACAA AGACCCCTGC AAGGCGGCTG     180
CCTTTCTTGG GGACATTGCC CTGGACGAAG AGGACCTGAG GGCCTTCCAG GTACAGCAGG     240
CTGTGGATCT CAGACGGCAC ACAGCTCGTA AGTCCTCCAT CAAAGCTGCA GTTCCAGGAA     300
ACACTTCTAC CCCCAGCTGC CAGAGCACCA ACGGGCAGCC TCAGAGGGGA GCCTGTGGGA     360
GATGGAGAGG TAGATCCCGT AGCCGGCGGG CGGCGACGTC CCGACCAGAG CGTGTGTGGC     420
CCGATGGGGT CATCCCCTTT GTCATTGGGG GAAACTTCAC TGGTAGCCAG AGGGCAGTCT     480
TCCGGCAGGC CATGAGGCAC TGGGAGAAGC ACACCTGTGT CACCTTCCTG GAGCGCACTG     540
ACGAGGACAG CTATATTGTG TTCACCTATC GACCTTGCGG GTGCTGCTCC TACGTGGGTC     600
GCCGCGGCGG GGGCCCCCAG GCCATCTCCA TCGGCAAGAA CTGTGACAAG TTCGGCATTG     660
TGGTCCACGA GCTGGGCCAC GTCGTCGGCT TCTGGCACGA ACACACTCGG CCAGACCGGG     720
ACCGCCACGT TTCCATCGTT CGTGAGAACA TCCAGCCAGG GCAGGAGTAT AACTTCCTGA     780
AGATGGAGCC TCAGGAGGTG GAGTCCCTGG GGGAGACCTA TGACTTCGAC AGCATCATGC     840
ATTACGCTCG GAACACATTC TCCAGGGGCA TCTTCCTGGA TACCATTGTC CCCAAGTATG     900
AGGTGAACGG GGTGAAACCT CCCATTGGCC AAAGGACACG GCTCAGCAAG GGGGACATTG     960
CCCAAGCCCG CAAGCTTTAC AAGTGCCCAG CCTGTGGAGA GACCCTGCAA GACAGCACAG    1020
GCAACTTCTC CTCCCCTGAA TACCCCAATG CTACTCTGC TCACATGCAC TGCGTGTGGC    1080
GCATCTCTGT CACACCCGGG GAGAAGATCA TCCTGAACTT CACGTCCCTG GACCTGTACC    1140
GCAGCCGCCT GTGCTGGTAC GACTATGTGG AGGTCCGAGA TGGCTTCTGG AGGAAGGCGC    1200
CCCTCCGAGG CCGCTTCTGC GGGTCCAAAC TCCCTGAGCC TATCGTCTCC ACTGACAGCC    1260
GCCTCTGGGT TGAATTCCGC AGCAGCAGCA ATTGGGTTGG AAAGGGCTTC TTTGCAGTCT    1320
ACGAAGCCAT CTGCGGGGGT GATGTGAAAA AGGACTATGG CCACATTCAA TCGCCCAACT    1380
ACCCAGACGA TTACCGGCCC AGCAAAGTCT GCATCTGGCG GATCCAGGTG TCTGAGGGCT    1440
TCCACGTGGG CCTCACATTC CAGTCCTTTG AGATTGAGCG CCACGACAGC TGTGCCTACG    1500
ACTATCTGGA GGTGCGCGAC GGGCACAGTG AGAGCAGCAC CCTCATCGGG CGCTACTGTG    1560
GCTATGAGAA GCCTGATGAC ATCAAGAGCA CGTCCAGCCG CCTCTGGCTC AAGTTCGTCT    1620
CTGACGGGTC CATTAACAAA GCGGGCTTTG CCGTCAACTT TTTCAAAGAG GTGGACGAGT    1680
GCTCTCGGCC CAACCGCGGG GGCTGTGAGC AGCGGTGCCT CAACACCCTG GGCAGCTACA    1740
AGTGCAGCTG TGACCCCGGG TACGAGCTGG CCCCAGACAA GCGCCGCTGT GAGGCTGCTT    1800
```

```
GTGGCGGATT  CCTCACCAAG  CTCAACGGCT  CCATCACCAG  CCCGGGCTGG  CCCAAGGAGT    1860

ACCCCCCCAA  CAAGAACTGC  ATCTGGCAGC  TGGTGGCCCC  CACCCAGTAC  CGCATCTCCC    1920

TGCAGTTTGA  CTTCTTTGAG  ACAGAGGGCA  ATGATGTGTG  CAAGTACGAC  TTCGTGGAGG    1980

TGCGCAGTGG  ACTCACAGCT  GACTCCAAGC  TGCATGGCAA  GTTCTGTGGT  TCTGAGAAGC    2040

CCGAGGTCAT  CACCTCCCAG  TACAACAACA  TGCGCGTGGA  GTTCAAGTCC  GACAACACCG    2100

TGTCCAAAAA  GGGCTTCAAG  GCCCACTTCT  TCTCAGAAAA  GAGGCCAGCT  CTGCAGCCCC    2160

CTCGGGGACG  CCCCCACCAG  CTCAAATTCC  GAGTGCAGAA  AAGAAACCGG  ACCCCCAGT     2220

GAGGCCTGCC  AGGCCTCCCG  GACCCCTTGT  TACTCAGGAA  CCTCACCTTG  GACGGAATGG    2280

GATGGGGGCT  TCGGTGCCCA  CCAACCCCCC  ACCTCCACTC  TGCCATTCCG  GCCCACCTCC    2340

CTCTGGCCGG  ACAGAACTGG  TGCTCTCTTC  TCCCCACTGT  GCCCGTCCGC  GGACCGGGGA    2400

CCCTTCCCCG  TGCCCTACCC  CCTCCCATTT  TGATGGTGTC  TGTGACATTT  CCTGTTGTGA    2460

AGTAAAAGAG  GGACCCCTGC  GTCCTGC                                          2487
```

( 2 ) INFORMATION FOR SEQ ID NO:2:

( i ) SEQUENCE CHARACTERISTICS:
        ( A ) LENGTH: 1547 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

```
GGGGACTTCT  TGAACTTGCA  GGGAGAATAA  CTTGCGCACC  CCACTTTGCG  CCGGTGCCTT    60

TGCCCCAGCG  GAGCCTGCTT  CGCCATCTCC  GAGCCCCACC  GCCCCTCCAC  TCCTCGGCCT    120

TGCCCGACAC  TGAGACGCTG  TTCCCAGCGT  GAAAAGAGAG  ACTGCGCGGC  CGGCACCCGG    180

GAGAAGGAGG  AGGCAAAGAA  AAGGAACGGA  CATTCGGTCC  TTGCGCCAGG  TCCTTTGACC    240

AGAGTTTTTC  CATGTGGACG  CTCTTTCAAT  GGACGTGTCC  CCGCGTGCTT  CTTAGACGGA    300

CTGCGGTCTC  CTAAAGGTCG  ACCATGGTGG  CCGGGACCCG  CTGTCTTCTA  GCGTTGCTGC    360

TTCCCCAGGT  CCTCCTGGGC  GGCGCGGCTG  GCCTCGTTCC  GGAGCTGGGC  CGCAGGAAGT    420

TCGCGGCGGC  GTCGTCGGGC  CGCCCCTCAT  CCCAGCCCTC  TGACGAGGTC  CTGAGCGAGT    480

TCGAGTTGCG  GCTGCTCAGC  ATGTTCGGCC  TGAAACAGAG  ACCCACCCCC  AGCAGGGACG    540

CCGTGGTGCC  CCCCTACATG  CTAGACCTGT  ATCGCAGGCA  CTCAGGTCAG  CCGGGCTCAC    600

CCGCCCCAGA  CCACCGGTTG  GAGAGGGCAG  CCAGCCGAGC  CAACACTGTG  CGCAGCTTCC    660

ACCATGAAGA  ATCTTTGGAA  GAACTACCAG  AAACGAGTGG  GAAAACAACC  GGAGATTCT     720

TCTTTAATTT  AAGTTCTATC  CCCACGGAGG  AGTTTATCAC  CTCAGCAGAG  CTTCAGGTTT    780

TCCGAGAACA  GATGCAAGAT  GCTTTAGGAA  ACAATAGCAG  TTTCCATCAC  CGAATTAATA    840

TTTATGAAAT  CATAAAACCT  GCAACAGCCA  ACTCGAAATT  CCCCGTGACC  AGACTTTTGG    900

ACACCAGGTT  GGTGAATCAG  AATGCAAGCA  GGTGGGAAAG  TTTTGATGTC  ACCCCCGCTG    960

TGATGCGGTG  GACTGCACAG  GGACACGCCA  ACCATGGATT  CGTGGTGGAA  GTGGCCCACT    1020

TGGAGGAGAA  ACAAGGTGTC  TCCAAGAGAC  ATGTTAGGAT  AAGCAGGTCT  TTGCACCAAG    1080

ATGAACACAG  CTGGTCACAG  ATAAGGCCAT  TGCTAGTAAC  TTTTGGCCAT  GATGGAAAAG    1140

GCATCCTCT  CCACAAAAGA  GAAAAACGTC  AAGCCAAACA  CAAACAGCGG  AAACGCCTTA     1200

AGTCCAGCTG  TAAGAGACAC  CCTTTGTACG  TGGACTTCAG  TGACGTGGGG  TGGAATGACT    1260

GGATTGTGGC  TCCCCCGGGG  TATCACGCCT  TTTACTGCCA  CGGAGAATGC  CCTTTTCCTC    1320
```

| TGGCTGATCA | TCTGAACTCC | ACTAATCATG | CCATTGTTCA | GACGTTGGTC | AACTCTGTTA | 1380 |
| ACTCTAAGAT | TCCTAAGGCA | TGCTGTGTCC | CGACAGAACT | CAGTGCTATC | TCGATGCTGT | 1440 |
| ACCTTGACGA | GAATGAAAAG | GTTGTATTAA | AGAACTATCA | GGACATGGTT | GTGGAGGGTT | 1500 |
| GTGGGTGTCG | CTAGTACAGC | AAAATTAAAT | ACATAAATAT | ATATATA | | 1547 |

(2) INFORMATION FOR SEQ ID NO:3:

(i) SEQUENCE CHARACTERISTICS:
      (A) LENGTH: 1774 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:3:

| AGATCTTGAA | AACACCCGGG | CCACACACGC | CGCGACCTAC | AGCTCTTTCT | CAGCGTTGGA | 60 |
| GTGGAGACGG | CGCCCGCAGC | GCCCTGCGCG | GGTGAGGTCC | GCGCAGCTGC | TGGGGAAGAG | 120 |
| CCCACCTGTC | AGGCTGCGCT | GGGTCAGCGC | AGCAAGTGGG | GCTGGCCGCT | ATCTCGCTGC | 180 |
| ACCCGGCCGC | GTCCCGGGCT | CCGTGCGCCC | TCGCCCCAGC | TGGTTTGGAG | TTCAACCCTC | 240 |
| GGCTCCGCCG | CCGGCTCCTT | GCGCCTTCGG | AGTGTCCCGC | AGCGACGCCG | GAGCCGACG | 300 |
| CGCCGCGCGG | GTACCTAGCC | ATGGCTGGGG | CGAGCAGGCT | GCTCTTTCTG | TGGCTGGGCT | 360 |
| GCTTCTGCGT | GAGCCTGGCG | CAGGGAGAGA | GACCGAAGCC | ACCTTTCCCG | GAGCTCCGCA | 420 |
| AGCTGTGCC | AGGTGACCGC | ACGGCAGGTG | GTGGCCCGGA | CTCCGAGCTG | CAGCCGCAAG | 480 |
| ACAAGGTCTC | TGAACACATG | CTGCGGCTCT | ATGACAGGTA | CAGCACGGTC | CAGGCGGCCC | 540 |
| GGACACCGGG | CTCCCTGGAG | GGAGGCTCGC | AGCCCTGGCG | CCCTCGGCTC | CTGCGCGAAG | 600 |
| GCAACACGGT | TCGCAGCTTT | CGGGCGGCAG | CAGCAGAAAC | TCTTGAAAGA | AAAGGACTGT | 660 |
| ATATCTTCAA | TCTGACATCG | CTAACCAAGT | CTGAAAACAT | TTTGTCTGCC | ACACTGTATT | 720 |
| TCTGTATTGG | AGAGCTAGGA | AACATCAGCC | TGAGTTGTCC | AGTGTCTGGA | GGATGCTCCC | 780 |
| ATCATGCTCA | GAGGAAACAC | ATTCAGATTG | ATCTTTCTGC | ATGGACCCTC | AAATTCAGCA | 840 |
| GAAACCAAAG | TCAACTCCTT | GGCCATCTGT | CAGTGGATAT | GGCCAAATCT | CATCGAGATA | 900 |
| TTATGTCCTG | GCTGTCTAAA | GATATCACTC | AATTCTTGAG | GAAGGCCAAA | GAAAATGAAG | 960 |
| AGTTCCTCAT | AGGATTTAAC | ATTACGTCCA | AGGGACGCCA | GCTGCCAAAG | AGGAGGTTAC | 1020 |
| CTTTTCCAGA | GCCTTATATC | TTGGTATATG | CCAATGATGC | CGCCATTTCT | GAGCCAGAAA | 1080 |
| GTGTGGTATC | AAGCTTACAG | GGACACCGGA | ATTTTCCCAC | TGGAACTGTT | CCCAAATGGG | 1140 |
| ATAGCCACAT | CAGAGCTGCC | CTTTCCATTG | AGCGGAGGAA | GAAGCGCTCT | ACTGGGGTCT | 1200 |
| TGCTGCCTCT | GCAGAACAAC | GAGCTTCCTG | GGCAGAATA | CCAGTATAAA | AGGATGAGG | 1260 |
| TGTGGGAGGA | GAGAAAGCCT | TACAAGACCC | TTCAGGCTCA | GGCCCCTGAA | AAGAGTAAGA | 1320 |
| ATAAAAAGAA | ACAGAGAAAG | GGGCCTCATC | GGAAGAGCCA | GACGCTCCAA | TTTGATGAGC | 1380 |
| AGACCCTGAA | AAAGGCAAGG | AGAAAGCAGT | GGATTGAACC | TCGGAATTGC | GCCAGGAGAT | 1440 |
| ACCTCAAGGT | AGACTTTGCA | GATATTGGCT | GGAGTGAATG | GATTATCTCC | CCCAAGTCCT | 1500 |
| TTGATGCCTA | TTATTGCTCT | GGAGCATGCC | AGTTCCCCAT | GCCAAAGTCT | TTGAAGCCAT | 1560 |
| CAAATCATGC | TACCATCCAG | AGTATAGTGA | GAGCTGTGGG | GGTCGTTCCT | GGGATTCCTG | 1620 |
| AGCCTTGCTG | TGTACCAGAA | AAGATGTCCT | CACTCAGTAT | TTTATTCTTT | GATGAAAATA | 1680 |
| AGAATGTAGT | GCTTAAAGTA | TACCCTAACA | TGACAGTAGA | GTCTTGCGCT | TGCAGATAAC | 1740 |

CTGGCAAAGA ACTCATTTGA ATGCTTAATT CAAT                                            1774

( 2 ) INFORMATION FOR SEQ ID NO:4:

( i ) SEQUENCE CHARACTERISTICS:
     ( A ) LENGTH: 1751 base pairs
     ( B ) TYPE: nucleic acid
     ( C ) STRANDEDNESS: double
     ( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
| GGCAGAGGAG | GAGGGAGGGA | GGGAAGGAGC | GCGGAGCCCG | GCCCGGAAGC | TAGGTGAGTG | 60
| TGGCATCCGA | GCTGAGGGAC | GCGAGCCTGA | GACGCCGCTG | CTGCTCCGGC | TGAGTATCTA | 120
| GCTTGTCTCC | CCGATGGGAT | TCCCGTCCAA | GCTATCTCGA | GCCTGCAGCG | CCACAGTCCC | 180
| CGGCCCTCGC | CCAGGTTCAC | TGCAACCGTT | CAGAGGTCCC | CAGGAGCTGC | TGCTGGCGAG | 240
| CCCGCTACTG | CAGGGACCTA | TGGAGCCATT | CCGTAGTGCC | ATCCCGAGCA | ACGCACTGCT | 300
| GCAGCTTCCC | TGAGCCTTTC | CAGCAAGTTT | GTTCAAGATT | GGCTGTCAAG | AATCATGGAC | 360
| TGTTATTATA | TGCCTTGTTT | TCTGTCAAGA | CACCATGATT | CCTGGTAACC | GAATGCTGAT | 420
| GGTCGTTTTA | TTATGCCAAG | TCCTGCTAGG | AGGCGCGAGC | CATGCTAGTT | TGATACCTGA | 480
| GACGGGGAAG | AAAAAAGTCG | CCGAGATTCA | GGGCCACGCG | GGAGGACGCC | GCTCAGGGCA | 540
| GAGCCATGAG | CTCCTGCGGG | ACTTCGAGGC | GACACTTCTG | CAGATGTTTG | GGCTGCGCCG | 600
| CCGCCCGCAG | CCTAGCAAGA | GTGCCGTCAT | TCCGGACTAC | ATGCGGGATC | TTTACCGGCT | 660
| TCAGTCTGGG | GAGGAGGAGG | AAGAGCAGAT | CCACAGCACT | GGTCTTGAGT | ATCCTGAGCG | 720
| CCCGGCCAGC | CGGGCCAACA | CCGTGAGGAG | CTTCCACCAC | GAAGAACATC | TGGAGAACAT | 780
| CCCAGGGACC | AGTGAAAACT | CTGCTTTTCG | TTTCCTCTTT | AACCTCAGCA | GCATCCCTGA | 840
| GAACGAGGTG | ATCTCCTCTG | CAGAGCTTCG | GCTCTTCCGG | GAGCAGGTGG | ACCAGGGCCC | 900
| TGATTGGGAA | AGGGGCTTCC | ACCGTATAAA | CATTTATGAG | GTTATGAAGC | CCCAGCAGA | 960
| AGTGGTGCCT | GGGCACCTCA | TCACACGACT | ACTGGACACG | AGACTGGTCC | ACCACAATGT | 1020
| GACACGGTGG | GAAACTTTTG | ATGTGAGCCC | TGCGGTCCTT | CGCTGGACCC | GGGAGAAGCA | 1080
| GCCAAACTAT | GGGCTAGCCA | TTGAGGTGAC | TCACCTCCAT | CAGACTCGGA | CCCACCAGGG | 1140
| CCAGCATGTC | AGGATTAGCC | GATCGTTACC | TCAAGGGAGT | GGGAATTGGG | CCCAGCTCCG | 1200
| GCCCCTCCTG | GTCACCTTTG | GCCATGATGG | CCGGGGCCAT | GCCTTGACCC | GACGCCGGAG | 1260
| GGCCAAGCGT | AGCCCTAAGC | ATCACTCACA | GCGGGCCAGG | AAGAAGAATA | AGAACTGCCG | 1320
| GCGCCACTCG | CTCTATGTGG | ACTTCAGCGA | TGTGGGCTGG | AATGACTGGA | TTGTGGCCCC | 1380
| ACCAGGCTAC | CAGGCCTTCT | ACTGCCATGG | GGACTGCCCC | TTTCCACTGG | CTGACCACCT | 1440
| CAACTCAACC | AACCATGCCA | TTGTGCAGAC | CCTGGTCAAT | TCTGTCAATT | CCAGTATCCC | 1500
| CAAAGCCTGT | TGTGTGCCCA | CTGAACTGAG | TGCCATCTCC | ATGCTGTACC | TGGATGAGTA | 1560
| TGATAAGGTG | GTACTGAAAA | ATTATCAGGA | GATGGTAGTA | GAGGGATGTG | GGTGCCGCTG | 1620
| AGATCAGGCA | GTCCTTGAGG | ATAGACAGAT | ATACACACCA | CACACACACA | CCACATACAC | 1680
| CACACACACA | CGTTCCCATC | CACTCACCCA | CACACTACAC | AGACTGCTTC | CTTATAGCTG | 1740
| GACTTTTATT | T | | | | | 1751

( 2 ) INFORMATION FOR SEQ ID NO:5:

( i ) SEQUENCE CHARACTERISTICS:
     ( A ) LENGTH: 2153 base pairs (B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:5:

```
CTGGTATATT TGTGCCTGCT GGAGGTGGAA TTAACAGTAA GAAGGAGAAA GGGATTGAAT      60
GGACTTACAG GAAGGATTTC AAGTAAATTC AGGGAAACAC ATTTACTTGA ATAGTACAAC     120
CTAGAGTATT ATTTTACACT AAGACGACAC AAAAGATGTT AAAGTTATCA CCAAGCTGCC     180
GGACAGATAT ATATTCCAAC ACCAAGGTGC AGATCAGCAT AGATCTGTGA TTCAGAAATC     240
AGGATTTGTT TTGGAAAGAG CTCAAGGGTT GAGAAGAACT CAAAAGCAAG TGAAGATTAC     300
TTTGGGAACT ACAGTTTATC AGAAGATCAA CTTTTGCTAA TTCAAATACC AAAGGCCTGA     360
TTATCATAAA TTCATATAGG AATGCATAGG TCATCTGATC AAATAATATT AGCCGTCTTC     420
TGCTACATCA ATGCAGCAAA AACTCTTAAC AACTGTGGAT AATTGGAAAT CTGAGTTTCA     480
GCTTTCTTAG AAATAACTAC TCTTGACATA TTCCAAAATA TTTAAAATAG GACAGGAAAA     540
TCGGTGAGGA TGTTGTGCTC AGAAATGTCA CTGTCATGAA AATAGGTAA ATTTGTTTTT      600
TCAGCTACTG GGAAACTGTA CCTCCTAGAA CCTTAGGTTT TTTTTTTTT AAGAGGACAA      660
GAAGGACTAA AAATATCAAC TTTTGCTTTT GGACAAAAAT GCATCTGACT GTATTTTAC      720
TTAAGGGTAT TGTGGGTTTC CTCTGGAGCT GCTGGGTTCT AGTGGGTTAT GCAAAGGAG      780
GTTGGGAGA CAATCATGTT CACTCCAGTT TTATTTATAG AAGACTACGG AACCACGAAA      840
GACGGGAAAT ACAAAGGGAA ATTCTCTCTA TCTTGGGTTT GCCTCACAGA CCCAGACCAT     900
TTTCACCTGG AAAACAAGCG TCCTCTGCAC CTCTCTTTAT GCTGGATCTC TACAATGCCA     960
TGACCAATGA AGAAAATCCT GAAGAGTCGG AGTACTCAGT AAGGGCATCC TTGGCAGAAG    1020
AGACCAGAGG GGCAAGAAAG GGATACCCAG CCTCTCCCAA TGGGTATCCT CGTCGCATAC    1080
AGTTATCTCG GACGACTCCT CTGACCACCC AGAGTCCTCC TCTAGCCAGC CTCCATGATA    1140
CCAACTTTCT GAATGATGCT GACATGGTCA TGAGCTTTGT CAACTTAGTT GAAAGAGACA    1200
AGGATTTTTC TCACCAGCGA AGGCATTACA AAGAATTTCG ATTTGATCTT ACCCAAATTC    1260
CTCATGGAGA GGCAGTGACA GCAGCTGAAT TCCGGATATA CAAGGACCGG AGCAACAACC    1320
GATTTGAAAA TGAAACAATT AAGATTAGCA TATATCAAAT CATCAAGGAA TACACAAATA    1380
GGGATGCAGA TCTGTTCTTG TTAGACACAA GAAAGGCCCA AGCTTTAGAT GTGGGTTGGC    1440
TTGTCTTTGA TATCACTGTG ACCAGCAATC ATTGGGTGAT TAATCCCCAG AATAATTTGG    1500
GCTTACAGCT CTGTGCAGAA ACAGGGGATG GACGCAGTAT CAACGTAAAA TCTGCTGGTC    1560
TTGTGGGAAG ACAGGGACCT CAGTCAAAAC AACCATTCAT GGTGGCCTTC TTCAAGGCGA    1620
GTGAGGTACT TCTTCGATCC GTGAGAGCAG CCAACAAACG AAAAAATCAA AACCGCAATA    1680
AATCCAGCTC TCATCAGGAC TCCTCCAGAA TGTCCAGTGT TGGAGATTAT AACACAAGTG    1740
AGCAAAAACA AGCCTGTAAG AAGCACGAAC TCTATGTGAG CTTCCGGGAT CTGGGATGGC    1800
AGGACTGGAT TATAGCACCA GAAGGATACG CTGCATTTTA TTGTGATGGA GAATGTTCTT    1860
TTCCACTTAA CGCCCATATG AATGCCACCA ACCACGCTAT AGTTCAGACT CTGGTTCATC    1920
TGATGTTTCC TGACCACGTA CCAAAGCCTT GTTGTGCTCC AACCAAATTA AATGCCATCT    1980
CTGTTCTGTA CTTTGATGAC AGCTCCAATG TCATTTTGAA AAAATATAGA AATATGGTAG    2040
TACGCTCATG TGGCTGCCAC TAATATTAAA TAATATTGAT AATAACAAAA AGATCTGTAT    2100
TAAGGTTTAT GGCTGCAATA AAAAGCATAC TTTCAGACAA ACAGAAAAAA AAA           2153
```

( 2 ) INFORMATION FOR SEQ ID NO:6:

( i ) SEQUENCE CHARACTERISTICS:
        ( A ) LENGTH: 2923 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---:|
| CGACCATGAG | AGATAAGGAC | TGAGGGCCAG | GAAGGGGAAG | CGAGCCCGCC | GAGAGGTGGC | 60 |
| GGGGACTGCT | CACGCCAAGG | GCCACAGCGG | CCGCGCTCCG | GCCTCGCTCC | GCCGCTCCAC | 120 |
| GCCTCGCGGG | ATCCGCGGGG | GCAGCCCGGC | CGGGCGGGGA | TGCCGGGGCT | GGGGCGGAGG | 180 |
| GCGCAGTGGC | TGTGCTGGTG | GTGGGGCTG | CTGTGCAGCT | GCTGCGGGCC | CCGCCGCTG | 240 |
| CGGCCGCCCT | TGCCCGCTGC | CGCGGCCGCC | GCCGCGGGG | GGCAGCTGCT | GGGGACGGC | 300 |
| GGGAGCCCCG | GCCGCACGGA | GCAGCCGCCG | CCGTCGCCGC | AGTCCTCCTC | GGGCTTCCTG | 360 |
| TACCGGCGGC | TCAAGACGCA | GGAGAAGCGG | GAGATGCAGA | AGGAGATCTT | GTCGGTGCTG | 420 |
| GGGCTCCCGC | ACCGGCCCCG | GCCCCTGCAC | GGCCTCCAAC | AGCCGCAGCC | CCGGCGCTC | 480 |
| CGGCAGCAGG | AGGAGCAGCA | GCAGCAGCAG | CAGCTGCCTC | GCGGAGAGCC | CCCTCCCGGG | 540 |
| CGACTGAAGT | CCGCGCCCCT | CTTCATGCTG | GATCTGTACA | ACGCCCTGTC | CGCCGACAAC | 600 |
| GACGAGGACG | GGCGTCGGA | GGGGAGAGG | CAGCAGTCCT | GGCCCCACGA | AGCAGCCAGC | 660 |
| TCGTCCCAGC | GTCGGCAGCC | GCCCCGGGC | GCCGCGCACC | CGCTCAACCG | CAAGAGCCTT | 720 |
| CTGGCCCCCG | GATCTGGCAG | CGGCGGCGCG | TCCCCACTGA | CCAGCGCGCA | GGACAGCGCC | 780 |
| TTCCTCAACG | ACGCGGACAT | GGTCATGAGC | TTTGTGAACC | TGGTGGAGTA | CGACAAGGAG | 840 |
| TTCTCCCCTC | GTCAGCGACA | CCACAAAGAG | TTCAAGTTCA | ACTTATCCCA | GATTCCTGAG | 900 |
| GGTGAGGTGG | TGACGGCTGC | AGAATTCCGC | ATCTACAAGG | ACTGTGTTAT | GGGGAGTTTT | 960 |
| AAAAACCAAA | CTTTTCTTAT | CAGCATTTAT | CAAGTCTTAC | AGGAGCATCA | GCACAGAGAC | 1020 |
| TCTGACCTGT | TTTTGTTGGA | CACCCGTGTA | GTATGGGCCT | CAGAAGAAGG | CTGGCTGGAA | 1080 |
| TTTGACATCA | CGGCCACTAG | CAATCTGTGG | GTTGTGACTC | CACAGCATAA | CATGGGGCTT | 1140 |
| CAGCTGAGCG | TGGTGACAAG | GGATGGAGTC | CACGTCCACC | CCGAGCCGC | AGGCCTGGTG | 1200 |
| GGCAGAGACG | GCCCTTACGA | TAAGCAGCCC | TTCATGGTGG | CTTTCTTCAA | AGTGAGTGAG | 1260 |
| GTCCACGTGC | GCACCACCAG | GTCAGCCTCC | AGCCGGCGCC | GACAACAGAG | TCGTAATCGC | 1320 |
| TCTACCCAGT | CCCAGGACGT | GGCGCGGGTC | TCCAGTGCTT | CAGATTACAA | CAGCAGTGAA | 1380 |
| TTGAAAACAG | CCTGCAGGAA | GCATGAGCTG | TATGTGAGTT | CCAAGACCT | GGGATGGCAG | 1440 |
| GACTGGATCA | TTGCACCCAA | GGGCTATGCT | GCCAATTACT | GTGATGGAGA | ATGCTCCTTC | 1500 |
| CCACTCAACG | CACACATGAA | TGCAACCAAC | CACGCGATTG | TGCAGACCTT | GGTTCACCTT | 1560 |
| ATGAACCCCG | AGTATGTCCC | CAAACCGTGC | TGTGCGCCAA | CTAAGCTAAA | TGCCATCTCG | 1620 |
| GTTCTTTACT | TTGATGACAA | CTCCAATGTC | ATTCTGAAAA | AATACAGGAA | TATGGTTGTA | 1680 |
| AGAGCTTGTG | GATGCCACTA | ACTCGAAACC | AGATGCTGGG | GACACACATT | CTGCCTTGGA | 1740 |
| TTCCTAGATT | ACATCTGCCT | TAAAAAAACA | CGGAAGCACA | GTTGGAGGTG | GGACGATGAG | 1800 |
| ACTTTGAAAC | TATCTCATGC | CAGTGCCTTA | TTACCCAGGA | AGATTTTAAA | GGACCTCATT | 1860 |
| AATAATTTGC | TCACTTGGTA | AATGACGTGA | GTAGTTGTTG | GTCTGTAGCA | AGCTGAGTTT | 1920 |
| GGATGTCTGT | AGCATAAGGT | CTGGTAACTG | CAGAAACATA | ACCGTGAAGC | TCTTCCTACC | 1980 |
| CTCCTCCCCC | AAAAACCCAC | CAAAATTAGT | TTTAGCTGTA | GATCAAGCTA | TTTGGGGTGT | 2040 |

| | | | | | |
|---|---|---|---|---|---|
| TTGTTAGTAA | ATAGGGAAAA | TAATCTCAAA | GGAGTTAAAT | GTATTCTTGG | CTAAAGGATC | 2100 |
| AGCTGGTTCA | GTACTGTCTA | TCAAAGGTAG | ATTTTACAGA | GAACAGAAAT | CGGGGAAGTG | 2160 |
| GGGGAACGC | CTCTGTTCAG | TTCATTCCCA | GAAGTCCACA | GGACGCACAG | CCCAGGCCAC | 2220 |
| AGCCAGGGCT | CCACGGGGCG | CCCTTGTCTC | AGTCATTGCT | GTTGTATGTT | CGTGCTGGAG | 2280 |
| TTTTGTTGGT | GTGAAAATAC | ACTTATTTCA | GCCAAAACAT | ACCATTTCTA | CACCTCAATC | 2340 |
| CTCCATTTGC | TGTACTCTTT | GCTAGTACCA | AAAGTAGACT | GATTACACTG | AGGTGAGGCT | 2400 |
| ACAAGGGGTG | TGTAACCGTG | TAACACGTGA | AGGCAGTGCT | CACCTCTTCT | TTACCAGAAC | 2460 |
| GGTTCTTTGA | CCAGCACATT | AACTTCTGGA | CTGCCGGCTC | TAGTACCTTT | TCAGTAAAGT | 2520 |
| GGTTCTCTGC | CTTTTACTA | TACAGCATAC | CACGCCACAG | GGTTAGAACC | AACGAAGAAA | 2580 |
| ATAAAATGAG | GGTGCCCAGC | TTATAAGAAT | GGTGTTAGGG | GGATGAGCAT | GCTGTTTATG | 2640 |
| AACGGAAATC | ATGATTTCCC | TGTAGAAAGT | GAGGCTCAGA | TTAAATTTTA | GAATATTTTC | 2700 |
| TAAATGTCTT | TTTCACAATC | ATGTGACTGG | GAAGGCAATT | TCATACTAAA | CTGATTAAAT | 2760 |
| AATACATTTA | TAATCTACAA | CTGTTTGCAC | TTACAGCTTT | TTTTGTAAAT | ATAAACTATA | 2820 |
| ATTTATTGTC | TATTTATAT | CTGTTTTGCT | GTGGCGTTGG | GGGGGGGGCC | GGGCTTTTGG | 2880 |
| GGGGGGGGGT | TTGTTTGGGG | GGTGTCGTGG | TGTGGGCGGG | CGG | | 2923 |

( 2 ) INFORMATION FOR SEQ ID NO:7:

( i ) SEQUENCE CHARACTERISTICS:
        ( A ) LENGTH: 1448 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| GTGACCGAGC | GGCGCGGACG | GCCGCCTGCC | CCCTCTGCCA | CCTGGGGCGG | TGCGGGCCCG | 60 |
| GAGCCCGGAG | CCCGGGTAGC | GCGTAGAGCC | GGCGCGATGC | ACGTGCGCTC | ACTGCGAGCT | 120 |
| GCGGCGCCGC | ACAGCTTCGT | GGCGCTCTGG | GCACCCCTGT | TCCTGCTGCG | CTCCGCCCTG | 180 |
| GCCGACTTCA | GCCTGGACAA | CGAGGTGCAC | TCGAGCTTCA | TCCACCGGCG | CCTCCGCAGC | 240 |
| CAGGAGCGGC | GGGAGATGCA | GCGCGAGATC | CTCTCCATTT | TGGGCTTGCC | CCACCGCCCG | 300 |
| CGCCCGCACC | TCCAGGGCAA | GCACAACTCG | GCACCCATGT | TCATGCTGGA | CCTGTACAAC | 360 |
| GCCATGGCGG | TGGAGGAGGG | CGGCGGGCCC | GGCGGCCAGG | GCTTCTCCTA | CCCCTACAAG | 420 |
| GCCGTCTTCA | GTACCCAGGG | CCCCCCTCTG | GCCAGCCTGC | AAGATAGCCA | TTTCCTCACC | 480 |
| GACGCCGACA | TGGTCATGAG | CTTCGTCAAC | CTCGTGGAAC | ATGACAAGGA | ATTCTTCCAC | 540 |
| CCACGCTACC | ACCATCGAGA | GTTCCGGTTT | GATCTTTCCA | AGATCCCAGA | AGGGGAAGCT | 600 |
| GTCACGGCAG | CCGAATTCCG | GATCTACAAG | GACTACATCC | GGGAACGCTT | CGACAATGAG | 660 |
| ACGTTCCGGA | TCAGCGTTTA | TCAGGTGCTC | CAGGAGCACT | TGGGCAGGGA | ATCGGATCTC | 720 |
| TTCCTGCTCG | ACAGCCGTAC | CCTCTGGGCC | TCGGAGGAGG | CTGGCTGGT | GTTTGACATC | 780 |
| ACAGCCACCA | GCAACCACTG | GGTGGTCAAT | CCGCGGCACA | ACCTGGGCCT | GCAGCTCTCG | 840 |
| GTGGAGACGC | TGGATGGGCA | GAGCATCAAC | CCCAAGTTGG | CGGGCCTGAT | TGGGCGGCAC | 900 |
| GGGCCCCAGA | ACAAGCAGCC | CTTCATGGTG | GCTTTCTTCA | AGGCCACGGA | GGTCCACTTC | 960 |
| CGCAGCATCC | GGTCCACGGG | GAGCAAACAG | CGCAGCCAGA | ACCGCTCCAA | GACGCCCAAG | 1020 |
| AACCAGGAAG | CCCTGCGGAT | GGCCAACGTG | GCAGAGAACA | GCAGCAGCGA | CCAGAGGCAG | 1080 |

| | | | | | | |
|---|---|---|---|---|---|---|
| GCCTGTAAGA | AGCACGAGCT | GTATGTCAGC | TTCCGAGACC | TGGGCTGGCA | GGACTGGATC | 1140 |
| ATCGCGCCTG | AAGGCTACGC | CGCCTACTAC | TGTGAGGGGG | AGTGTGCCTT | CCCTCTGAAC | 1200 |
| TCCTACATGA | ACGCCACCAA | CCACGCCATC | GTGCAGACGC | TGGTCCACTT | CATCAACCCG | 1260 |
| GAAACGGTGC | CCAAGCCCTG | CTGTGCGCCC | ACGCAGCTCA | ATGCCATCTC | CGTCCTCTAC | 1320 |
| TTCGATGACA | GCTCCAACGT | CATCCTGAAG | AAATACAGAA | ACATGGTGGT | CCGGGCCTGT | 1380 |
| GGCTGCCACT | AGCTCCTCCG | AGAATTCAGA | CCCTTTGGGG | CCAAGTTTTT | CTGGATCCTC | 1440 |
| CATTGCTC | | | | | | 1448 |

What is claimed is:

1. A method of generating new bone growth in a mammal in need of such treatment comprising administrating to the mammal a bone morphogenetic protein (herein, "BMP") in combination with a Vitamin D compound, wherein the BMP is BMP-2 or BMP-4, and wherein:
   a. when the bone morphogenetic protein is BMP-2, from about 500 ng to about 1000 ng BMP-2 is administered in combination with about 6 ng of the Vitamin D compound; and
   b. when the bone morphogenetic protein is BMP-4, about 62.5 ng BMP-4 is administered in combination with about 6 ng of the Vitamin D compound.

2. The method of claim 1 wherein the BMP is BMP-2 and the Vitamin D compound is 1,25 dihydroxy Vitamin $D_3$.

3. The method of claim 2 wherein about 500 ng of BMP-2 is administered in combination with about 6 ng of 1,25 dihydroxy Vitamin $D_3$.

4. The method of claim 2 wherein about 1000 ng of BMP-2 is administered in combination with about 6 ng of 1,25 dihydroxy Vitamin $D_3$.

5. The method of claim 1 wherein the BMP is BMP-4 and the Vitamin D compound is 1,25 dihydroxy Vitamin $D_3$.

6. The method of claim 1 wherein the administration of the Vitamin D compound and the BMP is by injection.

7. The method of claim 1 wherein the administration of the Vitamin D compound and the BMP is topical-oral.

8. The method of claim 1 wherein the administration of the Vitamin D compound is oral and the administration of the BMP is by injection.

9. A composition for generating new bone growth in a mammal in need of such treatment, the composition comprising:
   a. a Vitamin D compound;
   b. a bone morphogenetic protein (herein, "BMP"), wherein the BMP is BMP-2 or BMP-4; and
   c. a pharmaceutically-acceptable carrier;
   wherein
   i. when the bone morphogenetic protein is BMP-2, from about 500 ng to about 1000 ng BMP-2 is administered in combination with about 6 ng of the Vitamin D compound; and
   ii. when the bone morphogenetic protein is BMP-4, about 62.5 ng BMP-4 is administered in combination with about 6 ng of the Vitamin D compound.

10. The composition of claim 9 wherein the BMP is BMP-2 and the Vitamin D compound is 1,25 dihydroxy Vitamin $D_3$.

11. The composition of claim 10 wherein about 500 ng of BMP-2 is administered in combination with about 6 ng of 1,25 dihydroxy Vitamin $D_3$.

12. The composition of claim 10 wherein about 1000 ng of BMP-2 is administered in combination with about 6 ng of 1,25 dihydroxy Vitamin $D_3$.

13. The composition of claim 10 wherein the pharmaceutically-acceptable carrier is an injectable carrier.

14. The composition of claim 10 wherein the pharmaceutically-acceptable carrier is a topical-oral carrier.

15. The composition of claim 9, wherein the BMP is BMP-4 and the Vitamin D compound is 1,25 dihydroxy Vitamin $D_3$.

* * * * *